(12) United States Patent
Moussa

(10) Patent No.: US 11,912,846 B2
(45) Date of Patent: *Feb. 27, 2024

(54) ADDITIVES FOR BUILD MATERIALS AND ASSOCIATED PRINTED 3D ARTICLES

(71) Applicant: 3D Systems, Inc., Rock Hill, SC (US)

(72) Inventor: Khalil Moussa, Rock Hill, SC (US)

(73) Assignee: 3D SYSTEMS, INC., Rock Hill, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/690,694

(22) Filed: Mar. 9, 2022

(65) Prior Publication Data

US 2022/0289942 A1    Sep. 15, 2022

Related U.S. Application Data

(60) Provisional application No. 63/159,133, filed on Mar. 10, 2021.

(51) Int. Cl.
*C08K 5/01*     (2006.01)
*B33Y 10/00*    (2015.01)
(Continued)

(52) U.S. Cl.
CPC ............. *C08K 5/01* (2013.01); *B29C 64/106* (2017.08); *B33Y 10/00* (2014.12); *B33Y 70/10* (2020.01); *C08F 20/10* (2013.01); *B29K 2033/04* (2013.01)

(58) Field of Classification Search
CPC ......... C08K 5/01; B29C 64/106; B33Y 10/00; B33Y 70/10; C08F 20/10; B29K 2033/04
See application file for complete search history.

(56) References Cited

U.S. PATENT DOCUMENTS

| 5,185,419 A | * | 2/1993 | Funk | .................. C08G 77/52 |
| | | | | 528/25 |
| 2018/0215933 A1 | | 8/2018 | Xu et al. | |
| 2022/0289984 A1 | * | 9/2022 | Moussa | .................. B29C 64/124 |

FOREIGN PATENT DOCUMENTS

| CH | 558768 A | * | 2/1975 | ........... C07C 309/00 |
| WO | 2015012229 | | 1/2015 | |
| WO | 2019071071 | | 4/2019 | |

OTHER PUBLICATIONS

English machine translation of CH 558768 (Year: 1975).*

(Continued)

*Primary Examiner* — Angela C Scott
(74) *Attorney, Agent, or Firm* — Maynard Nexsen PC; John P. Zimmer

(57) ABSTRACT

Additives for three-dimensional build materials or inks are described herein which, in some embodiments, can impart flame retardant properties and/or structural enhancements to articles printed from the build materials. In some embodiments, such an additive comprises a compound of Formula I herein, wherein L and Z are ring substituents comprising at least one polymerizable point of unsaturation, and wherein $R^1$ and $R^2$ are independently selected from the group consisting of alkylene and alkenylene, and $R^3$-$R^6$ each represent one to four optional ring substituents, each one of the one to four ring substituents independently selected from the group consisting of alkyl, heteroalkyl, haloalkyl, halo, hydroxyl, alkoxy, amine, amide, and ether, and wherein n is an integer from 1 to 7.

28 Claims, 1 Drawing Sheet

(51) Int. Cl.
*B29C 64/106* (2017.01)
*B33Y 70/10* (2020.01)
*C08F 20/10* (2006.01)
*B29K 33/04* (2006.01)

(56) References Cited

OTHER PUBLICATIONS

PCT International Search Report for PCT Application No. PCT/US2022/019427, dated Jun. 17, 2022 (5 pages).
PCT Written Opinion for PCT Application No. PCT/US2022/019427, dated Jun. 17, 2022 (5 pages).

\* cited by examiner

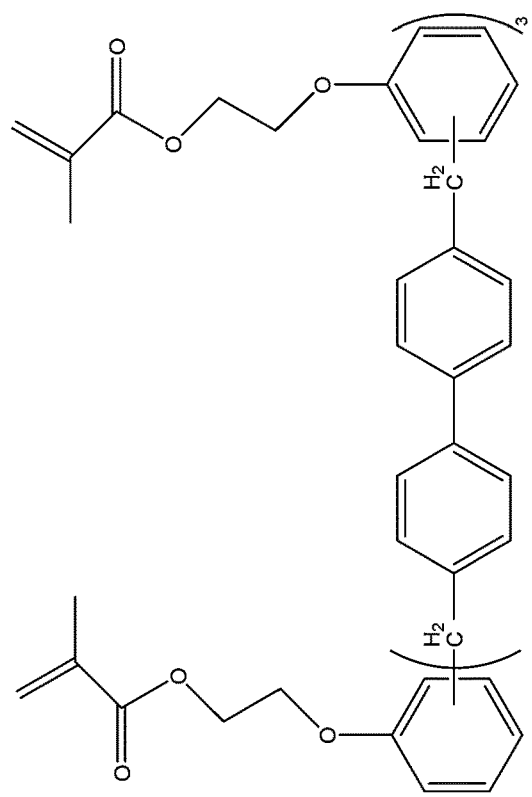
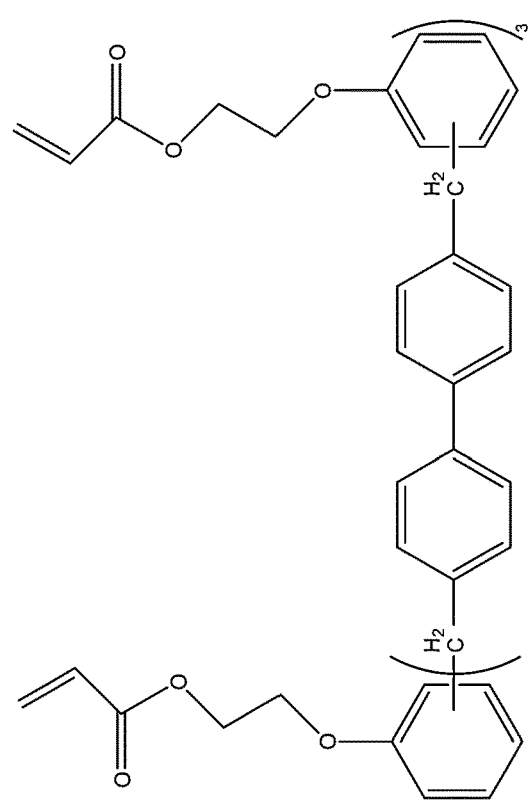

ADDITIVES FOR BUILD MATERIALS AND ASSOCIATED PRINTED 3D ARTICLES

CROSS REFERENCE TO RELATED APPLICATIONS

This application claims priority pursuant to 35 U.S.C. § 119 to U.S. Provisional Patent Application No. 63/159,133, filed Mar. 10, 2021, which is hereby incorporated by reference in its entirety.

FIELD

The present invention relates to additives for three-dimensional build materials and, in particular, to additives that can impart flame retardant properties and/or structural enhancements to articles printed from the build materials.

BACKGROUND 3D printers employ build materials, which are also known as inks, to form various 3D objects, articles, or parts in accordance with computer generated files. In some instances, the build material is solid at ambient temperatures and converts to liquid at elevated jetting temperatures. In other instances, the build material is liquid at ambient temperatures.

Build materials can comprise a variety of chemical species. Selection of chemical species to include in a build material can be selected according to various considerations including, but not limited to, desired chemical and/or mechanical properties of the printed article and operating parameters of the 3D printing apparatus. For example, ultra-violet (UV) curable acrylate formulations generally can print parts with high resolution on DLP systems. However, in many cases, the resulting parts lack desirable mechanical properties and can be prone to fracture or other degradative pathways. Such degradative pathways compromise article performance, leading to premature failure.

Additionally, some build materials and resultant articles printed from the build materials can be unsuitable for high temperature applications and/or other applications necessitating combustion resistance. As a result, 3D printing technology may find limited application in fields requiring flame resistant or flame retardant materials and articles.

SUMMARY

In view of the foregoing, additives for three-dimensional build materials or inks are described herein which, in some embodiments, can impart flame retardant properties and/or structural enhancements to articles printed from the build materials. In one aspect, an additive described herein is a compound of Formula I:

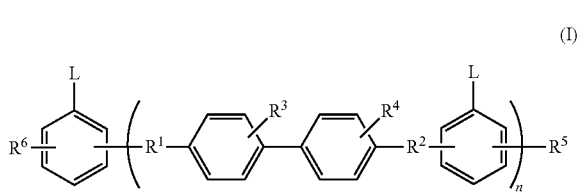

(I)

wherein L and Z are ring substituents comprising at least one polymerizable point of unsaturation, and wherein $R^1$ and $R^2$ are independently selected from the group consisting of alkylene and alkenylene, and $R^3$-$R^6$ each represent one to four optional ring substituents, each one of the one to four ring substituents independently selected from the group consisting of alkyl, heteroalkyl, haloalkyl, halo, hydroxyl, alkoxy, amine, amide, and ether, and wherein n is an integer from 1 to 7 or from 1 to 5. It is understood that hydrogen occupies positions on the aryl rings of Formula I in the absence of optional substituents $R^3$-$R^6$.

In another aspect, polymerizable liquids are provided comprising additives of Formula I described herein. In some embodiments, the polymerizable liquids impart flame resistant and/or flame retardant properties to articles printed from the liquids. The polymerizable liquids may also impart desirable mechanical properties to the articles. A polymerizable liquid, in some embodiments, comprises at least one additive of Formula I, and an acrylate component. In some embodiments, the polymerizable liquid comprises a plurality of additives falling under the generic structure of Formula I. Moreover, the acrylate component can comprise acrylate monomer, acrylate oligomer, or mixtures thereof.

Additionally, methods of printing three-dimensional articles are described herein. A method, in some embodiments, comprises providing a polymerizable liquid comprising at least one additive of Formula I herein and an acrylate component. The polymerizable liquid is printed and cured to form the article. In some embodiments, the article is formed via a layer-by-layer process, wherein layer formation is administered via deposition and curing of a layer of the polymerizable liquid. The acrylate component can comprise acrylate monomer, acrylate oligomer, or mixtures thereof.

As described further herein, the polymerizable liquid may further comprise a photoinitiator component, and curing of the polymerizable liquid may occur by irradiation of the liquid with light of the appropriate wavelength to initial free radical polymerization.

These and other embodiments are further described in the following detailed description.

BRIEF DESCRIPTION OF THE DRAWINGS

FIG. 1 illustrates compounds of Formula I, according to some embodiments.

DETAILED DESCRIPTION

Embodiments described herein can be understood more readily by reference to the following detailed description and examples. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

The terms "three-dimensional printing system," "three-dimensional printer," "printing," and the like generally describe various solid freeform fabrication techniques for making three-dimensional articles or objects by selective deposition, jetting, fused deposition modeling, multijet modeling, and other additive manufacturing techniques now known in the art or that may be known in the future that use a build material or ink to fabricate three-dimensional objects.

In one aspect, an additive described herein is a compound of Formula I:

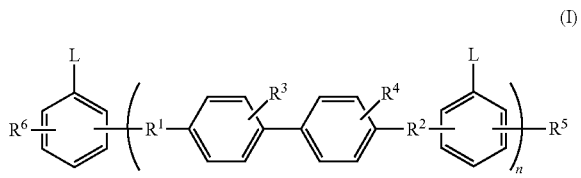

wherein L and Z are ring substituent comprising at least one polymerizable point of unsaturation, and wherein $R^1$ and $R^2$ are independently selected from the group consisting of alkylene and alkenylene, and $R^3$-$R^6$ each represent one to four optional ring substituents, each one of the one to four ring substituents independently selected from the group consisting of alkyl, heteroalkyl, haloalkyl, halo, hydroxyl, alkoxy, amine, amide, and ether, and wherein n is an integer from 1 to 7 or from 1 to 5. It is understood that hydrogen occupies positions on the aryl rings of Formula I in the absence of optional substituents $R^3$-$R^6$.

In certain implementations, one or both of the alkylene or alkenylene moieties $R^1$ and/or $R^2$ can have a carbon chain length of 1-8 carbon atoms, such as 1-5 carbon atoms, 1-3 carbon atoms, or 4-5 carbon atoms. In some embodiments, $R^1$ and/or $R^2$ comprises a C1-C10, C1-C8, or C1-05 alkylene or alkenylene, where a "Cn" species (e.g., a "Cn" alkylene or alkenylene moiety) includes exactly "n" carbon atoms in the species (e.g., a "C5" species contains exactly 5 carbon atoms).

As used herein, an alkylene moiety is a linear or branched saturated hydrocarbon moiety, such as an "ethylene" (—$CH_2CH_2$—) moiety. An alkenylene moiety is a linear or branched hydrocarbon moiety that includes one carbon-carbon double bond, such as a "propenylene" (—$CH_2CH$=$CH$—) moiety.

In some embodiments, L and Z comprise one or more moieties or functional groups independently selected from the group consisting of vinyl, vinyl ether, allyl, acrylate, and methacrylate. Moreover, in some embodiments, L and/or Z can comprise a cyclopolymerizable moiety or functional group. For example, L and/or Z may comprise a cyclopolymerizable moiety or functionality of the formula:

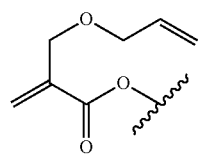

where ∿∿ is an attachment point of the cyclopolymerizable moiety or functionality to the compound of Formula I. In some embodiments, a compound of Formula I has a structure illustrated in FIG. 1.

In some embodiments, compounds of Formula 1 can impart desirable mechanical properties to articles printed with build materials or polymerizable liquids comprising a compound of Formula I. In some embodiments, for example, compounds of Formula I can increase heat deflection temperatures (HDT) of articles printed from polymerizable liquids comprising the compound(s). Additionally, compounds of Formula I can impart flame resistant and/or flame retardant properties to articles printed from polymerizable liquids comprising the compound(s).

In another aspect, polymerizable liquids are provided comprising additives of Formula I described herein. In some embodiments, the polymerizable liquids impart flame resistant and/or flame retardant properties to articles printed from the liquids. The polymerizable liquids may also impart desirable mechanical properties to the articles. A polymerizable liquid, in some embodiments, comprises an additive of Formula I, and an acrylate component. The acrylate component can comprise acrylate monomer, acrylate oligomer, or mixtures thereof.

One or more additives of Formula I can be present in a polymerizable liquid in any desired amount. Amount of an additive of Formula I in the polymerizable liquid can be selected according to several considerations including, but not limited to, desired mechanical properties and/or flame resistant properties of articles printed from the polymerizable liquid, and chemical identities and/or amounts of other species in the polymerizable liquid. In some embodiments, one or more additives of Formula I are present in a polymerizable liquid in a total amount of 5 to 40 wt. % or 10 to 30 wt. %, based on total weight of the polymerizable liquid.

As described herein, a polymerizable liquid can comprise an acrylate component in addition to the additive of Formula I. The acrylate component can comprise one or a mixture of light polymerizable acrylate species. In some embodiments, for example, the acrylate component can comprise acrylate monomer, acrylate oligomer, or mixtures thereof. As known to the skilled artisan, a monomer is a single structural unit of a polymer or copolymer and is not an oligomer or polymer. In contrast, an oligomer comprises a plurality of chemically linked monomers. In some embodiments, the acrylate component can comprise monofunctional acrylates, difunctional acrylates, or mixtures thereof. In some embodiments, for instance, the acrylate component comprises methyl (meth)acrylate, ethyl (meth)acrylate, n-propyl (meth)acrylate, n-butyl (meth)acrylate, isobutyl (meth)acrylate, n-hexyl (meth)acrylate, 2-ethylhexyl (meth)acrylate, n-octyl (meth)acrylate, n-decyl (meth)acrylate, n-dodecyl (meth)acrylate, 2-hydroxyethyl (meth)acrylate, 2- or 3-hydroxypropyl (meth)acrylate, 2-methoxyethyl (meth)acrylate, 2-ethoxyethyl (meth)acrylate, 2- or 3-ethoxypropyl (meth)acrylate, tetrahydrofurfuryl methacrylate, isobornyl (meth)acrylate, 2-(2-ethoxyethoxy)ethyl acrylate, cyclohexyl methacrylate, 2-phenoxyethyl acrylate, glycidyl acrylate, isodecyl acrylate, 2-phenoxyethyl (meth)acrylate, lauryl methacrylate, or mixtures thereof. In some embodiments, the acrylate component comprises a monofunctional or difunctional aliphatic urethane (meth)acrylate, or a monofunctional or difunctional polyether urethane (meth)acrylate.

The acrylate component, in some embodiments, can comprise one or more of allyl acrylate, allyl methacrylate, triethylene glycol di(meth)acrylate, tricyclodecane dimethanol diacrylate, and cyclohexane dimethanol diacrylate. Additionally, in some embodiments, the acrylate component comprises diacrylate and/or dimethacrylate esters of aliphatic, cycloaliphatic or aromatic diols, including 1,3- or 1,4-butanediol, neopentyl glycol, 1,6-hexanediol, diethylene glycol, triethylene glycol, tetraethylene glycol, polyethylene glycol, tripropylene glycol, ethoxylated or propoxylated neopentyl glycol, 1,4-dihydroxymethylcyclohexane, 2,2-bis (4-hydroxycyclohexyl)propane or bis(4-hydroxycyclohexyl)methane, hydroquinone, 4,4'-dihydroxybiphenyl, bisphenol A, bisphenol F, bisphenol S, ethoxylated or propoxylated bisphenol A, ethoxylated or propoxylated bisphenol F or ethoxylated or propoxylated bisphenol S.

Additional non-limiting examples of species suitable for inclusion in the acrylate component comprise the following: isobornyl acrylate (IBOA), commercially available from SARTOMER under the trade name SR 506A; difunctional acrylate commercially available from SARTOMER under the SR 833S trade designation; trifunctional acrylate monomer commercially available from SARTOMER under the SR 533 trade designation; isobornyl methacrylate, commercially available from SARTOMER under the trade name SR 423A; alkoxylated tetrahydrofurfuryl acrylate, commercially available from SARTOMER under the trade name SR 611; monofunctional urethane acrylate, commercially available from RAHN USA under the trade name GENOMER 1122; aliphatic urethane diacrylate, commercially available from ALLNEX under the trade name EBECRYL 8402; difunctional aliphatic urethane (meth)acrylate, commercially available from DYMAX under the BR-952 trade designation; triethylene glycol diacrylate, commercially available from SARTOMER under the trade name SR 272; and triethylene glycol dimethacrylate, commercially available from SARTOMER under the trade name SR 205. Other commercially available curable components may also be used. In addition, in some cases, a monofunctional or difunctional acrylate comprises an aliphatic polyester urethane acrylate oligomer, a urethane (meth)acrylate resin, and/or an acrylate amine oligomeric resin, such as EBECRYL 7100. In some embodiments, the acrylate component comprises one or more acrylate derivatives such as acryloylmorpholine.

In addition to the monofunctional and difunctional acrylate species components described above, it is also possible, in some cases, to include trifunctional or higher functional acrylate species in a polymerizable liquid described herein. For example, in some instances, one or more tri(meth) acrylates may be used. However, it is to be understood that the functionality (i.e., mono-, di-, tri-, or higher functionality) and the molecular weight of the acrylate species described herein can be selected to provide a build material having a viscosity suitable for use in a desired 3D printing system. Non-limiting examples of trifunctional or higher (meth)acrylates that may be suitable for use in some embodiments described herein include 1,1-trimethylolpropane tri(meth)acrylate, ethoxylated or propoxylated 1,1,1-trimethylolpropanetri(meth)acrylate, ethoxylated or propoxylated glycerol tri(meth)acrylate, pentaerythritol monohydroxy tri(meth)acrylate, dipentaerythritol monohydroxy penta(meth)acrylate, bis(trimethylolpropane) and tetra(meth)acrylate.

The acrylate component can be present in the polymerizable liquid in any amount consistent with the objectives described herein. In some embodiments, the acrylate component is present in an amount in an amount up to about 80 wt. %. For example, the acrylate component can be present in an amount of 30-70 wt. %, or 40-60 wt. %, based on total weight of the polymerizable liquid.

A polymerizable liquid described herein, can further comprise a photoinitiator component for initiating polymerization of one or more components of the liquid upon exposure to light of the proper wavelength. In some embodiments, the photoinitiator component can initiate polymerization of the additive of Formula I comprising one or more points of unsaturation polymerizable via free radical mechanisms. Similarly, a photoinitiator can be employed to polymerize the acrylate component. In some embodiments, the additive of Formula I can be copolymerized with the acrylate component. In other embodiments, the additive of Formula I and acrylate component are polymerized independently.

Any photoinitiator not inconsistent with the objectives of the present disclosure can be used. In some embodiments, a photoinitiator comprises an alpha-cleavage type (unimolecular decomposition process) photoinitiator or a hydrogen abstraction photosensitizer-tertiary amine synergist, operable to absorb light preferably between about 250 nm and about 420 nm or between about 300 nm and about 385 nm, to yield free radical(s).

Examples of alpha cleavage photoinitiators are Irgacure 184 (CAS 947-19-3), Irgacure 369 (CAS 119313-12-1), and Irgacure 819 (CAS 162881-26-7). An example of a photosensitizer-amine combination is Darocur BP (CAS 119-61-9) with diethylaminoethylmethacrylate.

In addition, in some instances, suitable photoinitiators comprise benzoins, including benzoin, benzoin ethers, such as benzoin methyl ether, benzoin ethyl ether and benzoin isopropyl ether, benzoin phenyl ether and benzoin acetate, acetophenones, including acetophenone, 2,2-dimethoxyacetophenone and 1,1-dichloroacetophenone, benzil, benzil ketals, such as benzil dimethyl ketal and benzil diethyl ketal, anthraquinones, including 2-methylanthraquinone, 2-ethylanthraquinone, 2-tert-butylanthraquinone, 1-chloroanthraquinone and 2-amylanthraquinone, triphenylphosphine, benzoylphosphine oxides, for example 2,4,6-trimethylbenzoyldiphenylphosphine oxide (Lucirin TPO), benzophenones, such as benzophenone and 4,4'-bis(N,N'-dimethylamino)benzophenone, thioxanthones and xanthones, acridine derivatives, phenazine derivatives, quinoxaline derivatives or 1-phenyl-1,2-propanedione, 2-O-benzoyl oxime, 1-aminophenyl ketones or 1-hydroxyphenyl ketones, such as 1-hydroxycyclohexyl phenyl ketone, phenyl 1-hydroxyisopropyl ketone and 4-isopropylphenyl 1-hydroxyisopropyl ketone.

Suitable photoinitiators can also comprise those operable for use with a HeCd laser radiation source, including acetophenones, 2,2-dialkoxybenzophenones and 1-hydroxyphenyl ketones, such as 1-hydroxycyclohexyl phenyl ketone or 2-hydroxyisopropyl phenyl ketone (=2-hydroxy-2,2-dimethylacetophenone). Additionally, in some cases, suitable photoinitiators comprise those operable for use with an Ar laser radiation source including benzil ketals, such as benzil dimethyl ketal. In some embodiments, a photoinitiator comprises an α-hydroxyphenyl ketone, benzil dimethyl ketal or 2,4,6-trimethylbenzoyldiphenylphosphine oxide or a mixture thereof.

Another class of suitable photoinitiators, in some instances, comprises ionic dye-counter ion compounds capable of absorbing actinic radiation and generating free radicals for polymerization initiation. In some embodiments, polymerizable liquids containing ionic dye-counter ion compounds can be polymerized upon exposure to visible light within the adjustable wavelength range of about 400 nm to about 700 nm. Ionic dye-counter ion compounds and their mode of operation are disclosed in EP-A-0 223 587 and U.S. Pat. Nos. 4,751,102; 4,772,530; and 4,772,541.

A photoinitiator can be present in a polymerizable liquid described herein in any amount not inconsistent with the objectives of the present disclosure. In some embodiments, a photoinitiator is present in an amount of up to about 5 wt. %, based on the total weight of the polymerizable liquid. In some cases, a photoinitiator is present in an amount ranging from about 0.1 wt. % to about 5 wt. %.

Moreover, in some embodiments, a polymerizable liquid described herein can further comprise one or more sensitizers. A sensitizer can be added to increase the effectiveness of one or more photoinitiators that may also be present. Any sensitizer not inconsistent with the objectives of the present disclosure may be used. In some cases, a sensitizer comprises isopropylthioxanthone (ITX) or 2-chlorothioxanthone (CTX).

A sensitizer can be present in the polymerizable liquid in any amount not inconsistent with the objectives of the present disclosure. In some embodiments, a sensitizer is present in an amount ranging from about 0.1 wt. % to about 2 wt. % or from about 0.5 wt. % to about 1 wt. %, based on the total weight of the polymerizable liquid.

In some embodiments, one or more UV-absorbers and/or light stabilizers can be present in the polymerizable liquid. In some embodiments, for example, one or more UV-absorbers and/or light stabilizers can be present in an amount of 0.1-2 wt. %, based on the total weight of the polymerizable liquid. In some embodiments, UV-absorbers and/or light stabilizers are commercially available from BASF of Florham Park, New Jersey under the TINUVIN® trade-designation.

Additionally, methods of printing three-dimensional articles are described herein. A method, in some embodiments, comprises providing a polymerizable liquid comprising an additive of Formula I and an acrylate component. The polymerizable liquid is printed and cured to form the article. In some embodiments, the article is formed via a layer-by-layer process, wherein layer formation is administered via deposition and curing of a layer of the polymerizable liquid. The acrylate component can comprise acrylate monomer, acrylate oligomer, or mixtures thereof.

As described further herein, the polymerizable liquid may further comprise a photoinitiator component, and curing of the polymerizable liquid may occur by irradiation of the liquid with light of the appropriate wavelength to initial free radical polymerization.

In some embodiments, layers of polymerizable liquids can be deposited according to an image of the 3D article in a computer readable format during formation of the three-dimensional article. The polymerizable liquid can be deposited according to preselected computer aided design (CAD) parameters. Moreover, in some cases, one or more layers of the polymerizable liquid described herein has a thickness of about 10 µm to about 100 µm, about 10 µm to about 80 µm, about 10 µm to about 50 µm, about 20 µm to about 100 µm, about 20 µm to about 80 µm, or about 20 µm to about 40 µm. Other thicknesses are also possible.

Additionally, it is to be understood that methods of printing a 3D article described herein can include so-called "multi-jet" or "stereolithography" 3D printing methods. For example, in some instances, a multi-jet method of printing a 3D article comprises selectively depositing layers of a polymerizable liquid described herein onto a substrate, such as a build pad of a 3D printing system. In addition, in some embodiments, a method described herein further comprises supporting at least one of the layers of the polymerizable liquid with a support material. Any support material not inconsistent with the objectives of the present disclosure may be used.

It is also possible to form a 3D article from a polymerizable liquid described herein using stereolithography. For example, in some cases, a method of printing a 3D article comprises retaining the polymerizable liquid in a container and selectively applying energy to the polymerizable liquid in the container to solidify at least a portion of a polymerizable liquid, thereby forming a solidified layer that defines a cross-section of the 3D article. Additionally, a method described herein can further comprise raising or lowering the solidified layer to provide a new or second layer of polymerizable liquid, followed by again selectively applying energy to the polymerizable liquid in the container to solidify at least a portion of the new or second polymerizable liquid that defines a second cross-section of the 3D article. Further, the first and second cross-sections of the 3D article can be bonded or adhered to one another in the z-direction (or build direction corresponding to the direction of raising or lowering recited above) by the application of the energy for solidifying the polymerizable liquid. Moreover, selectively applying energy to the polymerizable liquid in the container can comprise applying electromagnetic radiation, such as UV and/or visible radiation, having a sufficient energy to initiate polymerization of the polymerizable material as described herein. In addition, in some cases, raising or lowering a solidified layer of polymerizable liquid is carried out using an elevator platform disposed in the container of fluid build material. A method described herein can also comprise planarizing a new layer of polymerizable liquid provided by raising or lowering an elevator platform. Such planarization can be carried out, in some cases, by a wiper or roller.

Articles printed according to methods described herein can exhibit one or more desirable mechanical properties. 3D articles printed from polymerizable liquids described herein may display a tensile modulus of at 2500-3000 MPa, in some embodiments. Values for tensile modulus provided herein can be determined according to ASTM D638. Additionally, 3D articles printed from polymerizable liquids described herein can exhibit a HDT of at least 100° C., such as 100-130° C. HDT is measured using DMA at 0.455 MPa according to ASTM D648.

Some non-limiting example embodiments described herein are provided below.

Embodiment 1. An additive of Formula I:

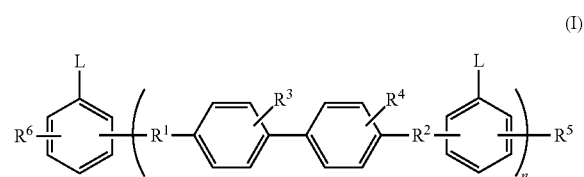

(I)

wherein L and Z are ring substituents comprising at least one polymerizable point of unsaturation, and wherein $R^1$ and $R^2$ are independently selected from the group consisting of alkylene and alkenylene, and $R^3$-$R^6$ each represent one to four optional ring substituents, each one of the one to four ring substituents independently selected from the group consisting of alkyl, heteroalkyl, haloalkyl, halo, hydroxyl, alkoxy, amine, amide, and ether, and wherein n is an integer from 1 to 7.

Embodiment 2. The additive of Embodiment 1, wherein $R^1$ and $R^2$ are alkylene.

Embodiment 3. The additive of Embodiment 1 or 2, wherein L and Z each comprise a moiety independently selected from the group consisting of vinyl, allyl, vinyl ether, acrylate, and methacrylate.

Embodiment 4. The additive of any of the preceding Embodiments, wherein L and Z each comprise a cyclopolymerizable functionality.

Embodiment 5. The additive of Embodiment 4, wherein the cyclopolymerizable functionality is of the formula:

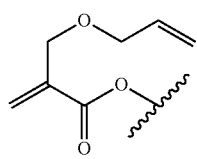 [SMILES: *OC(=O)C(=C)COCC=C]

where ∼∼∼ is an attachment point of the cyclopolymerizable functionality to the compound of Formula I.

Embodiment 6. The additive of any of the preceding Embodiments, wherein n is 2 or 3.

Embodiment 7. The additive of Embodiment 3, wherein L and Z each comprise an acrylate moiety.

Embodiment 8. The additive of Embodiment 3, wherein and L and Z each comprise a methacrylate moiety.

Embodiment 9. A polymerizable liquid comprising:
at least one additive of Formula I:

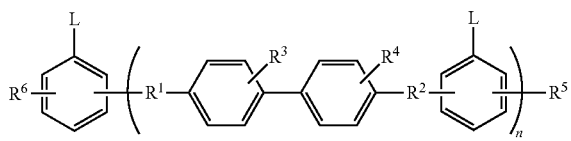

(I)

wherein L and Z are ring substituents comprising at least one polymerizable point of unsaturation, and wherein $R^1$ and $R^2$ are independently selected from the group consisting of alkylene and alkenylene, and $R^3$-$R^6$ each represent one to four optional ring substituents, each one of the one to four ring substituents independently selected from the group consisting of alkyl, heteroalkyl, haloalkyl, halo, hydroxyl, alkoxy, amine, amide, and ether, and wherein n is an integer from 1 to 7.

Embodiment 10. The polymerizable liquid of Embodiment 9, wherein $R^1$ and $R^2$ are alkylene.

Embodiment 11. The polymerizable liquid of Embodiment 9 or 10, wherein L and Z each comprise a moiety independently selected from the group consisting of vinyl, allyl, vinyl ether, acrylate, and methacrylate.

Embodiment 12. The polymerizable liquid of any of Embodiments 9-10, wherein L and Z each comprise a cyclopolymerizable functionality.

Embodiment 13. The polymerizable liquid of Embodiment 12, wherein the cyclopolymerizable functionality is of the formula:

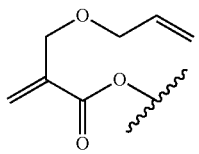 [SMILES: *OC(=O)C(=C)COCC=C]

where ∼∼∼ is an attachment point of the cyclopolymerizable moiety or functionality to the compound of Formula I.

Embodiment 14. The polymerizable liquid of any of Embodiments 9-13, wherein n is 2 or 3.

Embodiment 15. The polymerizable liquid of Embodiment 14, wherein L and Z each comprise an acrylate moiety.

Embodiment 16. The polymerizable liquid of Embodiment 14, wherein and L and Z each comprise a methacrylate moiety.

Embodiment 17. The polymerizable liquid of any of Embodiments 9-16, wherein the additive is present in an amount of 5-40 wt. % based on total weight of the polymerizable liquid.

Embodiment 18. The polymerizable liquid of any of Embodiments 9-16, wherein the additive is present in an amount of 10-30 wt. % based on total weight of the polymerizable liquid.

Embodiment 19. The polymerizable liquid of any of Embodiments 9-18 further comprising an acrylate component.

Embodiment 20. The polymerizable liquid of Embodiment 19, wherein the acrylate component acrylate monomer, acrylate oligomer, or mixtures thereof.

Embodiment 21. The polymerizable liquid of Embodiment 19 or 20, wherein the acrylate component is present in an amount of 30-70 wt. % based on total weight of the polymerizable liquid.

Embodiment 22. A method of printing a three-dimensional article comprising:
providing a polymerizable liquid comprising:
an acrylate component; and
at least one additive of Formula I:

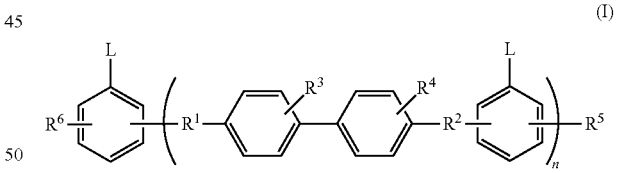

(I)

wherein L and Z are ring substituents comprising at least one polymerizable point of unsaturation, and wherein $R^1$ and $R^2$ are independently elected from the group consisting of alkylene and alkenylene, and $R^3$-$R^6$ each represent one to four optional ring substituents, each one of the one to four ring substituents independently selected from the group consisting of alkyl, heteroalkyl, haloalkyl, halo, hydroxyl, alkoxy, amine, amide, and ether, and wherein n is an integer from 1 to 7; and
printing and curing the polymerizable liquid with light to form the article.

Embodiment 23. The method of Embodiment 22, wherein the at least one additive is present in an amount of 5-40 wt. %, based on total weight of the polymerizable liquid.

Embodiment 24. The method of Embodiment 22 or 23, wherein the acrylate component is present in an amount of 30-70 wt. %, based on total weight of the polymerizable liquid.

Embodiment 25. The method of any of Embodiments 22-24, wherein L and Z each comprise a moiety independently selected from the group consisting of vinyl, allyl, vinyl ether, acrylate, and methacrylate.

Embodiment 26. The method of any of Embodiments 22-24, wherein L and Z each comprise a cyclopolymerizable functionality.

Embodiment 27. The method of Embodiment 26, wherein the cyclopolymerizable functionality is of the formula:

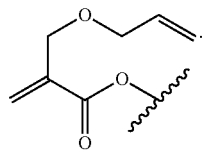 [SMILES: *OC(=O)C(=C)COCC=C]

Embodiment 28. The method of any of Embodiments 22-24, wherein L and Z each comprise an acrylate moiety.

Embodiment 29. The method of any of Embodiments 22-24, wherein and L and Z each comprise a methacrylate moiety.

All patent documents referred to herein are incorporated by reference in their entireties. Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. An additive of Formula I:

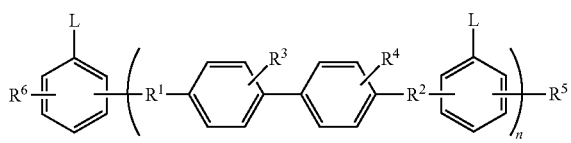

wherein L and Z are ring substituents comprising at least one polymerizable point of unsaturation, and wherein $R^1$ and $R^2$ are alkylene, and $R^3$-$R^6$ each represent one to four optional ring substituents, each one of the one to four ring substituents independently selected from the group consisting of alkyl, heteroalkyl, haloalkyl, halo, hydroxyl, alkoxy, amine, amide, and ether, and wherein n is an integer from 1 to 7.

2. The additive of claim 1, wherein L and Z each comprise a moiety independently selected from the group consisting of vinyl, allyl, vinyl ether, acrylate, and methacrylate.

3. An additive of Formula I:

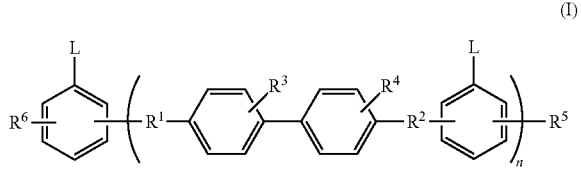

wherein L and Z are ring substituents comprising at least one polymerizable point of unsaturation, and wherein $R^1$ and $R^2$ are independently selected from the group consisting of alkylene and alkenylene, and $R^3$-$R^6$ each represent one to four optional ring substituents, each one of the one to four ring substituents independently selected from the group consisting of alkyl, heteroalkyl, haloalkyl, halo, hydroxyl, alkoxy, amine, amide, and ether, wherein n is an integer from 1 to 7, and wherein L and Z each comprise a cyclopolymerizable functionality.

4. The additive of claim 3, wherein the cyclopolymerizable functionality is of the formula:

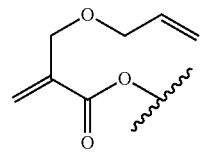 [SMILES: *OC(=O)C(=C)COCC=C]

where ⌇⌇⌇ is an attachment point of the cyclopolymerizable functionality to the compound of Formula I.

5. An additive of Formula I:

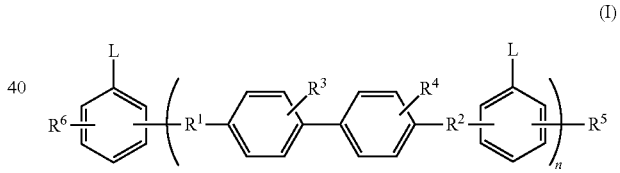

wherein L and Z are ring substituents comprising at least one polymerizable point of unsaturation, and wherein $R^1$ and $R^2$ are independently selected from the group consisting of alkylene and alkenylene, and $R^3$-$R^6$ each represent one to four optional ring substituents, each one of the one to four ring substituents independently selected from the group consisting of alkyl, heteroalkyl, haloalkyl, halo, hydroxyl, alkoxy, amine, amide, and ether, and wherein n is 2 or 3.

6. An additive of Formula I:

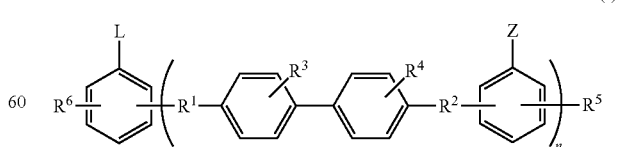

wherein L and Z are ring substituents comprising at least one polymerizable point of unsaturation, and wherein $R^1$ and $R^2$ are independently selected from the group consisting of alkylene and alkenylene, and $R^3$-$R^6$ each represent one to four optional ring substituents, each one of the one to four ring substituents independently selected from the group consisting of alkyl, heteroalkyl, haloalkyl, halo, hydroxyl, alkoxy, amine, amide, and ether, wherein n is an integer from 1 to 7, and wherein L and Z each comprise an acrylate moiety.

7. An additive of Formula I:

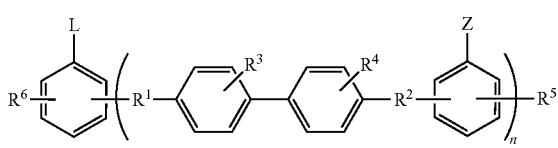

(I)

wherein L and Z are ring substituents comprising at least one polymerizable point of unsaturation, and wherein $R^1$ and $R^2$ are independently selected from the group consisting of alkylene and alkenylene, and $R^3$-$R^6$ each represent one to four optional ring substituents, each one of the one to four ring substituents independently selected from the group consisting of alkyl, heteroalkyl, haloalkyl, halo, hydroxyl, alkoxy, amine, amide, and ether, wherein n is an integer from 1 to 7, and wherein L and Z each comprise a methacrylate moiety.

8. A polymerizable liquid comprising:
   at least one additive of Formula I:

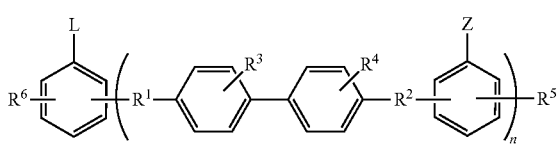

(I)

wherein L and Z are ring substituents comprising at least one polymerizable point of unsaturation, and wherein $R^1$ and $R^2$ are independently selected from the group consisting of alkylene and alkenylene, and $R^3$-$R^6$ each represent one to four optional ring substituents, each one of the one to four ring substituents independently selected from the group consisting of alkyl, heteroalkyl, haloalkyl, halo, hydroxyl, alkoxy, amine, amide, and ether, and wherein n is an integer from 1 to 7.

9. The polymerizable liquid of claim 8, wherein $R^1$ and $R^2$ are alkylene.

10. The polymerizable liquid of claim 8, wherein L and Z each comprise a moiety independently selected from the group consisting of vinyl, allyl, vinyl ether, acrylate, and methacrylate.

11. The polymerizable liquid of claim 8, wherein L and Z each comprise a cyclopolymerizable functionality.

12. The polymerizable liquid of claim 11, wherein the cyclopolymerizable functionality is of the formula:

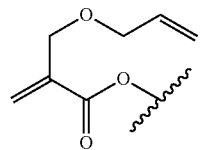

where $\sim\!\sim\!\sim$ is an attachment point of the cyclopolymerizable moiety or functionality to the compound of Formula I.

13. The polymerizable liquid of claim 8, wherein n is 2 or 3.

14. The polymerizable liquid of claim 13, wherein L and Z each comprise an acrylate moiety.

15. The polymerizable liquid of claim 13, wherein L and Z each comprise a methacrylate moiety.

16. The polymerizable liquid of claim 8, wherein the additive is present in an amount of 5-40 wt. % based on total weight of the polymerizable liquid.

17. The polymerizable liquid of claim 8, wherein the additive is present in an amount of 10-30 wt. % based on total weight of the polymerizable liquid.

18. The polymerizable liquid of claim 8 further comprising an acrylate component.

19. The polymerizable liquid of claim 18, wherein the acrylate component is an acrylate monomer, acrylate oligomer, or mixtures thereof.

20. The polymerizable liquid of claim 18, wherein the acrylate component is present in an amount of 30-70 wt. % based on total weight of the polymerizable liquid.

21. A method of printing a three-dimensional article comprising:
   providing a polymerizable liquid comprising:
      an acrylate component; and
      the additive of claim 1;
   printing and curing the polymerizable liquid with light to form the article.

22. The method of claim 21, wherein the additive is present in an amount of 5-40 wt. %, based on total weight of the polymerizable liquid.

23. The method of claim 21, wherein the acrylate component is present in an amount of 30-70 wt. %, based on total weight of the polymerizable liquid.

24. The method of claim 21, wherein L and Z each comprise a moiety independently selected from the group consisting of vinyl, allyl, vinyl ether, acrylate, and methacrylate.

25. The method of claim 21, wherein L and Z each comprise a cyclopolymerizable functionality.

26. The method of claim 25, wherein the cyclopolymerizable functionality is of the formula:

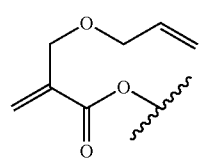

where $\sim\!\sim\!\sim$ is an attachment point of the cyclopolymerizable moiety or functionality to the compound of Formula I.

27. The method of claim 21, wherein L and Z each comprise an acrylate moiety.

28. The method of claim 21, wherein and L and Z each comprise a methacrylate moiety.

* * * * *